US012422852B2

(12) United States Patent
Henseleit et al.

(10) Patent No.: US 12,422,852 B2
(45) Date of Patent: Sep. 23, 2025

(54) WHEELCHAIR SYSTEM AND METHOD OF USE (71) Applicant: The Braun Corporation, Winamac, IN (US)

(72) Inventors: Andrew Henseleit, LaPorte, IN (US); John Hayes, Rochester, IN (US)

(73) Assignee: The Braun Corporation, Winamac, IN (US)

( * ) Notice: Subject to any disclaimer, the term of this patent is extended or adjusted under 35 U.S.C. 154(b) by 424 days.

(21) Appl. No.: 17/236,190

(22) Filed: Apr. 21, 2021

(65) Prior Publication Data

US 2021/0333796 A1 Oct. 28, 2021

Related U.S. Application Data (60) Provisional application No. 63/014,823, filed on Apr. 24, 2020.

(51) Int. Cl.
G05D 1/00 (2024.01)
A61G 3/02 (2006.01)
(Continued)

(52) U.S. Cl.
CPC ............ *G05D 1/0225* (2013.01); *A61G 3/02* (2013.01); *A61G 3/0808* (2013.01); *A61G 5/047* (2013.01);
(Continued)

(58) Field of Classification Search
CPC .. G05D 1/0225; G05D 1/0011; G05D 1/0276; G05D 2201/0206; A61G 3/02;
(Continued)

(56) References Cited

U.S. PATENT DOCUMENTS 5,489,170 A 2/1996 Inoue et al.
2009/0214314 A1 8/2009 Girardin et al.
(Continued)

FOREIGN PATENT DOCUMENTS

CN 110812018 A 2/2020
EP 3545929 A1 10/2019
(Continued)

OTHER PUBLICATIONS

KIPO International Searching Authority, Republic of Korea; International Search Report and The Written Opinion of the International Search Authority; Mail date: Jul. 28, 2021; pp. 1-10.
(Continued)

Primary Examiner — Anne Marie Antonucci
Assistant Examiner — Jodi Jones
(74) Attorney, Agent, or Firm — Daniel Tallitsch; Tyler Schultz (57) ABSTRACT A wheelchair system may include vehicles including docking systems for a wheelchair. The wheelchair and the docking system may be coupled to controllers in communication with one another via a secure communication channel. A user may use a computing device to send signals to and receive signals from the controllers and a data processing system to select the docking system to which the wheelchair may be secured.

23 Claims, 3 Drawing Sheets (51) Int. Cl.
  *A61G 3/08* (2006.01)
  *A61G 5/04* (2013.01)
  *A61G 5/10* (2006.01)
  *B60R 25/00* (2013.01)
  *H04L 9/08* (2006.01)
  *H04W 4/40* (2018.01)
  *H04W 12/037* (2021.01)
  *H04W 12/08* (2021.01)
  *H04W 76/10* (2018.01)

(52) U.S. Cl.
  CPC ............... *A61G 5/10* (2013.01); *B60R 25/00* (2013.01); *G05D 1/0011* (2013.01); *G05D 1/0276* (2013.01); *H04L 9/0819* (2013.01); *H04W 4/40* (2018.02); *H04W 12/037* (2021.01); *H04W 12/08* (2013.01); *H04W 76/10* (2018.02)

(58) Field of Classification Search
  CPC ........ A61G 3/0808; A61G 5/047; A61G 5/10; A61G 5/1029; A61G 2203/40; A61G 2205/60; B60R 25/00; H04L 9/0819; H04L 9/0861; H04L 2209/80; H04L 2209/84; H04W 4/40; H04W 12/037; H04W 12/08; H04W 76/10; H04W 4/80; H04W 12/03; H04W 12/50; G16H 40/60
  USPC ......... 701/2, 23, 1, 36, 25, 24, 22, 26, 31.4, 701/117, 300, 301, 408, 28, 3, 49, 41, 701/532, 50, 29.6, 70, 29.1, 400, 45, 701/31.5, 517, 33.4, 410, 533, 93, 32.6, 701/468, 469, 118, 465, 32.3, 414, 48, 701/119, 423, 120, 467, 34.3, 409, 411, 701/99, 32.7, 472, 484, 537, 27, 420, 96, 701/115, 16, 516, 519, 302, 33.2, 522, 701/19, 29.2, 32.4, 34.4, 4, 424, 51, 9, 701/29.3, 470, 482, 14, 431, 486, 451, 701/466, 523, 538, 79, 100, 32.2, 34.2, 701/425, 412, 445, 521, 525, 114, 124, 701/15, 32.1, 421, 446, 46, 485, 491, 701/514, 526, 53, 69, 10, 101, 102, 112, 701/13, 418, 430, 453, 494, 501, 540, 701/107, 30.6, 32.5, 32.9, 42, 461, 495, 701/5, 518, 52, 528, 103, 108, 116, 29.4, 701/29.7, 32.8, 33.3, 416, 437, 438, 442, 701/444, 447, 448, 460, 462, 471, 473, 701/487, 498, 515, 520, 527, 530, 534, 701/541, 33.7, 33.9, 34.1, 37, 434, 439, 701/30.8
  See application file for complete search history.

(56) References Cited

U.S. PATENT DOCUMENTS

| | | | |
|---|---|---|---|
| 2010/0020975 A1* | 1/2010 | Bissett | H04W 12/50 380/283 |
| 2019/0133852 A1 | 5/2019 | Ghannam et al. | |
| 2020/0077264 A1* | 3/2020 | Studer | H04L 63/105 |
| 2020/0104770 A1* | 4/2020 | Aich | B60N 2/245 |
| 2020/0113755 A1* | 4/2020 | Seko | H04M 1/04 |
| 2020/0323713 A1* | 10/2020 | Girardin | A61G 3/0808 |
| 2021/0100701 A1* | 4/2021 | Pedersen | B62D 65/02 |
| 2021/0275368 A1* | 9/2021 | Nagata | B60N 2/0273 |

FOREIGN PATENT DOCUMENTS

| | | | | |
|---|---|---|---|---|
| KR | 10-2013-0090550 A | 8/2013 | | |
| KR | 10-2016-0099424 A | 8/2016 | | |
| WO | 2015164147 A1 | 10/2015 | | |
| WO | WO-2018184884 A1 * | 10/2018 | | A61G 3/08 |
| WO | 2019017845 A1 | 1/2019 | | |
| WO | 2019027408 A1 | 2/2019 | | |

OTHER PUBLICATIONS

European Patent Office, Extended Search Report for EP Appl. No. 21792562.7, Dated Mar. 27, 2024, 14 pages.

* cited by examiner

WHEELCHAIR SYSTEM AND METHOD OF USE

RELATED APPLICATIONS

This application claims the benefit of U.S. Provisional Patent Application Ser. No. 63/014,823, filed Apr. 24, 2020 and entitled "Wheelchair System and Method of Use," the disclosure of which is hereby incorporated by reference in its entirety.

FIELD OF THE DISCLOSURE

The present application relates to a passenger vehicle for transporting one or more passengers, and more particularly to a docking system for a wheelchair on the passenger vehicle.

BACKGROUND

Automobile manufacturers do not currently mass-produce passenger motor vehicles specifically designed to transport passengers having physical limitations. Consequently, mass-produced passenger vehicles are modified, or retrofitted, by a number of aftermarket companies dedicated to supplying vehicles for physically limited passengers. Such vehicles can be modified by altering or adding certain parts or structures within a vehicle to accommodate the physically limited passenger.

What is needed is a better docking system to secure the wheelchair during transit and a system and method for facilitating communication between the docking system, a computing device, and/or the wheelchair.

SUMMARY

In an illustrative embodiment, a wheelchair system comprises: a wheelchair having a unique identifier associated therewith; a wheelchair controller operatively coupled to the wheelchair; a vehicle including an interior, a floor, and a docking system positioned in the interior and coupled to the floor, wherein the docking system includes a coupler mechanism and an actuator configured to adjust the height of the coupler mechanism relative to the floor; a dock controller operatively coupled to the docking system; a computing device separate from the wheelchair and the vehicle; and a data processing system configured to communicate with the dock controller and the computing device; wherein the computing device is configured to: (a) send the unique identifier associated with the wheelchair to the data processing system, and (b) send a signal to the data processing system indicating that the docking system has been selected; and wherein the dock controller is configured to: (a) receive from the data processing system the unique identifier associated with the wheelchair, (b) operatively connect to the wheelchair controller when the wheelchair is within a threshold proximity of the docking system, (c) send an encryption key to the wheelchair controller associated with a secure communication channel between the wheelchair controller and the dock controller, (d) send a signal to the actuator of the docking system to adjust the height of the coupler mechanism relative to the floor based on a signal received from the wheelchair controller through the secure communication channel.

In some embodiments, the unique identifier comprises at least one of: a name of the wheelchair, a pairing code associated with the wheelchair, and a MAC address associated with the wheelchair. In some embodiments, the dock controller is configured to operatively connect to the wheelchair controller via a wireless communication network.

In some embodiments, the wheelchair further includes: a set of wheels configured to rest on the floor of the vehicle, a bottom surface supported above the floor by the set of wheels, and a coupling device positioned on the bottom surface of the wheelchair; wherein a clearance distance is defined between the coupling device and the floor; and wherein the clearance distance is adjustable.

In some embodiments, the signal received from the wheelchair controller through the secure communication channel is a signal indicative of the clearance distance between the coupling device and the floor. In some embodiments, the coupling device of the wheelchair is configured to engage the coupler mechanism of the docking system when the wheelchair is secured to the docking system. In some embodiments, the dock controller is configured to send a signal to the actuator of the docking system to reduce the height of the coupler mechanism relative to the floor, after the coupler mechanism of the docking system is engaged with the coupling device of the wheelchair, to further secure the wheelchair to the docking system.

In some embodiments, the dock controller is configured to send a signal to the data processing system indicating that the docking system is not selectable. In some embodiments, the wheelchair is configured to engage and disengage with the docking system; and after the wheelchair is disengaged from the docking system, the dock controller is configured to send a signal to the data processing system indicating that the docking system from which the wheelchair disengaged is selectable.

In some embodiment, the docking system is one of a plurality of docking systems of the vehicle; the vehicle is one of a plurality of vehicles each having a plurality of docking systems; and the computing device is configured to display each of the plurality of docking systems of each of the pluralities of vehicles.

In another illustrative embodiment, a method of operation for a wheelchair system comprises: sending a unique identifier associated with a wheelchair to a data processing system; receiving, with a dock controller that is operatively coupled to a docking system for the wheelchair, the unique identifier associated with the wheelchair; sending an encryption key to a wheelchair controller operatively coupled to the wheelchair, wherein the encryption key is associated with a secure communication channel between the wheelchair controller and the dock controller; and adjusting the height of the docking system based on a signal received from the wheelchair controller through the secure communication channel.

In some embodiments, the method further comprises: operatively connecting the dock controller with the wheelchair controller via a wireless communication network, subsequent to receiving the unique identifier and prior to sending the encryption key to the wheelchair controller.

In some embodiments, the method further comprises: sending a signal to a computing device to request authorization for connecting the dock controller with wheelchair controller via the wireless communication network, prior to operatively connecting the dock controller with the wheelchair controller via the wireless communication network.

In some embodiments, the method further comprises: selecting the docking system with a computing device; sending a signal to the data processing system to indicate that the docking system was selected; and indicating that the selected docking system is no longer selectable.

In some embodiments, the wheelchair includes a set of wheels configured to rest on a floor of a vehicle, a bottom surface supported above the floor by the set of wheels, and a coupling device positioned on the bottom surface of the wheelchair; and the signal received from the wheelchair controller through the secure communication channel is a signal indicative of a clearance distance defined between the coupling device and the floor.

In some embodiments, the method further comprises: securing the wheelchair to the docking system; securing the wheelchair to the docking system includes: engaging a coupler mechanism of the docking system with the coupling device of the wheelchair; and reducing the height of the docking system, after the coupler mechanism of the docking system is engaged with the coupling device of the wheelchair, to reduce the clearance distance defined between the coupling device and the floor.

In some embodiments, the method further comprises: adjusting the clearance distance defined between the coupling device and the floor.

In some embodiments, the method further comprises: securing the wheelchair to the docking system; operatively connecting the dock controller with the wheelchair controller via a wireless communication network, subsequent to receiving the unique identifier and prior to sending the encryption key to the wheelchair controller; and sending signals indicative of the clearance distance through the secure communication channel, continuously, while the wheelchair is operatively connected to the docking system.

In some embodiments, the method further comprises: securing the wheelchair to the docking system; disengaging the wheelchair and the docking system; and sending a signal to the data processing system to indicate that the docking system from which the wheelchair was disengaged is available to be selected.

In another illustrative embodiment, a method of operation of a docking system for a wheelchair comprising: receiving, with a dock controller operatively coupled to the docking system, a unique identifier associated with the wheelchair; sending an encryption key to a wheelchair controller operatively coupled to the wheelchair, wherein the encryption key is associated with a secure communication channel between the wheelchair controller and the dock controller; adjusting the height of the docking system based on a signal received from the wheelchair controller through the secure communication channel.

BRIEF DESCRIPTION OF THE DRAWINGS

The above-mentioned aspects of the present disclosure and the manner of obtaining them will become more apparent and the disclosure itself will be better understood by reference to the following description of the embodiments of the disclosure, taken in conjunction with the accompanying drawings, wherein.

DETAILED DESCRIPTION

The embodiments of the present disclosure described below are not intended to be exhaustive or to limit the disclosure to the precise forms disclosed in the following detailed description. Rather, the embodiments are chosen and described so that others skilled in the art may appreciate and understand the principles and practices of the present disclosure.

Figure 1:
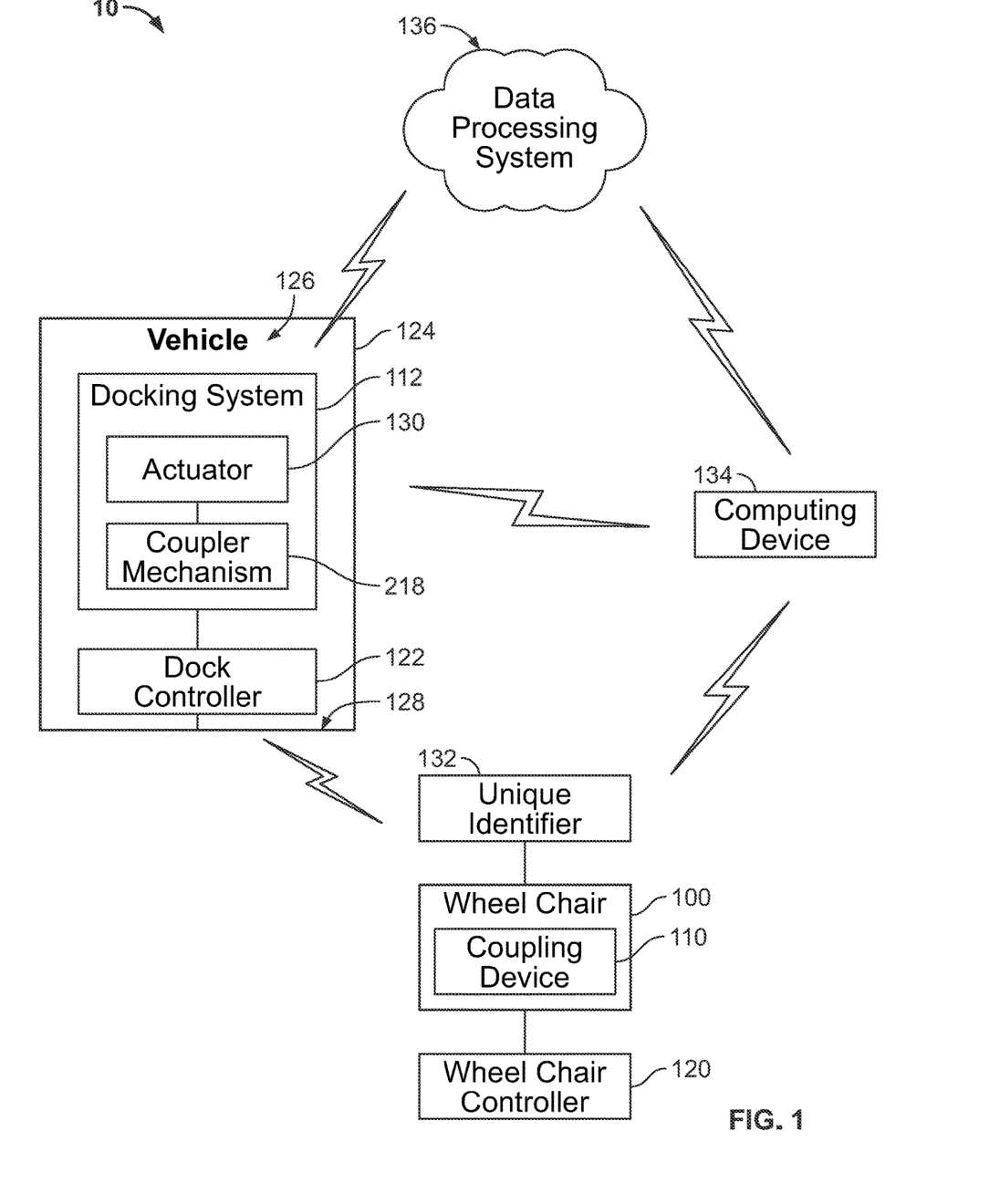
FIG. 1 is a diagrammatic view of a passenger vehicle including a docking system, a wheelchair, a computing device, and a data processing system.

FIG. 1 illustrates diagrammatically a wheelchair system 10 including a wheelchair 100 and a docking system 112. Components of the wheelchair system 10 (including by non-limiting example the wheelchair 100 and the docking system 112) are described in U.S. Provisional Application No. 62/866,064, which is incorporated by reference herein in its entirety.

As shown in FIG. 1, the wheelchair system 10 includes a wheelchair controller 120 operatively coupled to the wheelchair 100 and a dock controller 122 operatively coupled to the docking system 112. The controllers 120, 122 may each include a memory and a processor. Each memory is capable of storing logic, algorithms, software, etc. for performing one or more tasks. Each memory may further store information, collect data, and receive information from other controllers, systems, and devices described herein and otherwise. Each processor may be capable of executing the logic, algorithms, software, etc stored on the memory. The controllers may be single controllers or pluralities of controllers as described below. Moreover, the wheelchair controller 120 may be remotely located from the wheelchair 100 and communicate with the wheelchair 100 over a wireless communication network. Moreover, the dock controller 122 may be remotely located from the docking system 112 and communicate with the docking system 112 over a wireless communication network.

The wheelchair controller 120 may be in communication with user controls which may be operated by an occupant of the wheelchair 100 or other user. In particular, a user may adjust, among other things, the height of the wheelchair 100 with the user controls as will be described in greater detail below.

The wheelchair system 10 further includes a vehicle 124. The vehicle 124 may be a public and/or private transit vehicle including but not limited to buses, trolleybuses, trams (or light rail) and passenger trains, rapid transit (metro/subway/underground, etc.) and ferries. In any event, the vehicle 124 includes an interior 126 for accommodating passengers during transit. The vehicle 124 further includes a floor 128 positioned in the interior 126. The docking system 112 is coupled to the floor 128 and adjustable relative thereto in the longitudinal direction via a track system and in the vertical direction via an actuator 130 as described in greater detail below. The actuator 130 may at times be referred to as a first actuator 334. In any event, the actuator 130 is configured to adjust the height of a coupler mechanism 218 of the docking system 112 relative to the floor 128 as described in greater detail below.

The wheelchair 100 includes a coupling device 110 configured to form a physical connection with the coupler mechanism 218 of the docking system 112 to secure the wheelchair 100 to the docking system 112. The wheelchair 100 further includes a unique identifier 132 associated with the wheelchair 100. The unique identifier 132 may be, for example, a name of the wheelchair 100, a pairing code associated with the wheelchair 100, and/or a MAC address associated with the wheelchair 100.

In some embodiments, the wheelchair system 10 includes a computing device 134 and a data processing system 136. The data processing system 136 may be a cloud or cloud-type memory and processing system, or other suitable system for sending and receiving signals to and from the computing device 134, the dock controller 122 and/or the wheelchair controller 120. The computing device 134 may be a mobile telephone, a smartphone, a workstation, a portable computing device, other computing devices such as a laptop, or a desktop computer, or another suitable system for sending and receiving signals to and from the wheelchair controller 120, the dock controller 122 and/or data processing system 136.

In operation of the wheelchair system 10, the dock controller 122 sends a signal to the data processing system 136 to indicate that the docking system 112 is available to be selected by a user of the wheelchair system 10. The docking system 112 may be available to be selected when no wheelchair is physically connected to the docking system 112 or at other times when a wheelchair is physically connected to the docking system 112. For example, the docking system 112 may be available to be selected subsequent to a wheelchair physically disconnecting from the docking system 112 or subsequent to an electronic connection between the dock controller 122 and the wheelchair controller 120 being disconnected, as will be described in greater detail below.

In some embodiments, the docking system 112 may be available to be selected by some users of the wheelchair system 10 but unavailable to be selected by other users of the wheelchair system 10. This is true even while a wheelchair is concurrently, physically connected to the docking system 112.

For example, the docking system 112 is coupled to the floor 128 of a vehicle 126, and the vehicle 126 is a bus, which stops at several stops along a bus route. If a first user occupying a first wheelchair 100a physically connected to the docking system 112 has indicated via a computing device 134a an intent to exit the vehicle 124 at a third stop along the bus route, and a second user occupying a second wheelchair 100b has indicated via a computing device 134b an intent to board the vehicle at the third or subsequent stop along the bus route, then the docking system 112 may be available to be selected by the second user. For a third user occupying a third wheelchair 100c and indicating intent to board the vehicle 124 at a second stop along the bus route, the docking system 112 is not available to be selected. This is because the wheelchair 100a occupied by the first user will not disconnect from the docking system 112 until the third stop along the bus route; therefore, the docking system 112 is not available for the user occupying the third wheelchair 100b at the second stop.

In some embodiments, the wheelchair controller 120 sends a signal indicative of the unique identifier 132 associated with the wheelchair 100 to the computing device 134. The computing device 134 sends a signal to the data processing system 136 indicative of the unique identifier 132. In some embodiments, the computing device 134 may be configured to operate an application whereby a memory of the data processing system 136 or a memory of the computing device 134 has previously received and now stores the unique identifier 132 associated with the wheelchair 100. In any event, the computing device 134 is configured to send a signal to the data processing system 136 to indicate that the docking system 112 has been selected by the user, and the selection is associated with the unique identifier 132 associated with the wheelchair 120 for which the selection was made.

The data processing system 136 is configured to send a signal indicative of the unique identifier 132 to the dock controller 122. The dock controller 122 is configured to receive the signal indicative of the unique identifier 132 from the data processing system 136. A user occupying the wheelchair 100 may enter the interior 126 of the vehicle 124. When the wheelchair 100 is within a threshold proximity of the docking system 112, the dock controller 122 operatively (i.e. electronically) connects to the wheelchair controller 120 via a wireless communication network. In some embodiments, this operative connection may be formed prior to the wheelchair 100 being located in the interior 126 of the vehicle 124. In some embodiments, the operative connection may be a Bluetooth connection. In some embodiments, the operative connection may be a WiFi connection. In some embodiments, the operative connection may be a ZigBee connection. In some embodiments, the operative connection may be a Near Field Communication (NFC) connection.

The dock controller 122 sends an encryption key to the wheelchair controller 120 or the computing device 134, and the encryption key is associated with a secure communication channel for the dock controller 122 and the wheelchair controller 120. It should be appreciated that the encryption key may be provided via the wireless communication network(s) described above. It should also be appreciated that in some embodiments, the secure communication channel is facilitated via the wireless communication network(s) described above (for example via Wi-Fi or Bluetooth).

In some embodiments, the encryption key may be visual encryption key such an RFID tag (or similar electronic display) on the wheelchair 100 or on the computing device 134 readable by an RFID scanner on the docking system 112. The encryption key may also be a pin or push notification displayed to the user via the computing device 134 or displayed on the docking system 112. The user may accept the push notification or input the pin into the computing device 134 or the docking system 112 to establish the secure communication channel between the dock controller 122 and the wheelchair controller 120. In any event, the encryption key is provided and confirmed via a first and second device, the first device being the docking system 112 and the second device being the wheel chair 100 and/or the computing device 134.

Subsequent to the dock controller 122 and the wheelchair controller 120 operatively connecting and establishing a secure communication channel, the dock controller 122 may receive clearance data from the wheelchair controller 120 associated with the wheelchair 100. The clearance data is indicative of a clearance distance, which is a distance defined between the coupling device 110 and the floor 128 or other ground surface. The clearance distance may be adjusted by a user of the wheelchair 100 or other user with the user controls. For example, the user may actuate the user controls, causing the wheelchair controller 120 send a signal to adjust the height of the bottom surface 116 of the wheelchair 100 relative to the floor 128 or other ground surface. Additionally, the clearance distance may be determined in part by the type or model of wheelchair used in connection with the wheelchair system 10.

The clearance data is sent through the secure communication channel. The clearance data may be sent and received as a continuous or semi-continuous stream of signals sent from the wheelchair controller 120 to the dock controller 122. A first signal sent from the wheelchair controller 120 may include a first clearance distance and a second signal sent from the wheelchair controller 120 may include a second clearance distance.

Subsequent to receiving at least the first signal indicative of the first clearance distance, the dock controller 122 sends a signal to the actuator 130 of the docking system 112 to adjust the height of the coupler mechanism 218 relative to the floor 128. Thus, the height adjustment of the coupler mechanism 218 occurs based on the signal received from the wheelchair controller 120 through the secure communication channel. As the wheelchair 100 approaches the docking system 112, additional clearance data may be sent to the dock controller 122 in the continuous stream of signals described above. The additional clearance data may include the second signal including the second clearance distance. As a result, the height of the coupler mechanism 218 may be adjusted in real time based on the continuous stream of signals so that the coupler mechanism is positioned at a sufficient height to receive the coupling device of the wheelchair 100. This may occur even as the wheelchair 100 approaches the docking system 112.

The methods of operation described above, including connection of the coupler mechanism 218 to the coupling device 110, will become more clear based on the description of components of the wheelchair 100 and the docking system 112 that is provided below.

The wheelchair 100 may include a frame 102 supported by one or more wheels 104. A brake or anti-tilt/tip mechanism 106 may be located at one or more wheels 104 for slowing down or keeping the wheels 104 from turning, if necessary. The wheelchair 100 may be a powered wheelchair or a manually-operated wheelchair. Any type of wheelchair 100 is applicable to the present disclosure. It should be appreciated that in some instances a first user may operate the computing device 134 on behalf of a second user who is occupying or positioned in the wheelchair 100.

In the present disclosure, the docking system 112 allows for the wheelchair 100 to have greater clearance between it and the floor 128 than with conventional wheelchair-securing designs. Moreover, the docking system 112 includes a first latching mechanism for coupling to a coupling device 110 on the wheelchair 100, and a second latching mechanism for coupling the wheelchair 100 to the vehicle floor 128 and preventing it from tilting to the left or right as the vehicle makes a turn. Thus, the present disclosure provides a better connection between the wheelchair 100 and the vehicle floor 128, and one which is safer over conventional docking systems. Further, the docking system 112 may include a track system 114 which allows the docking system 112 to be adjusted longitudinally along the vehicle floor 128 for different sized passengers.

Figure 2:
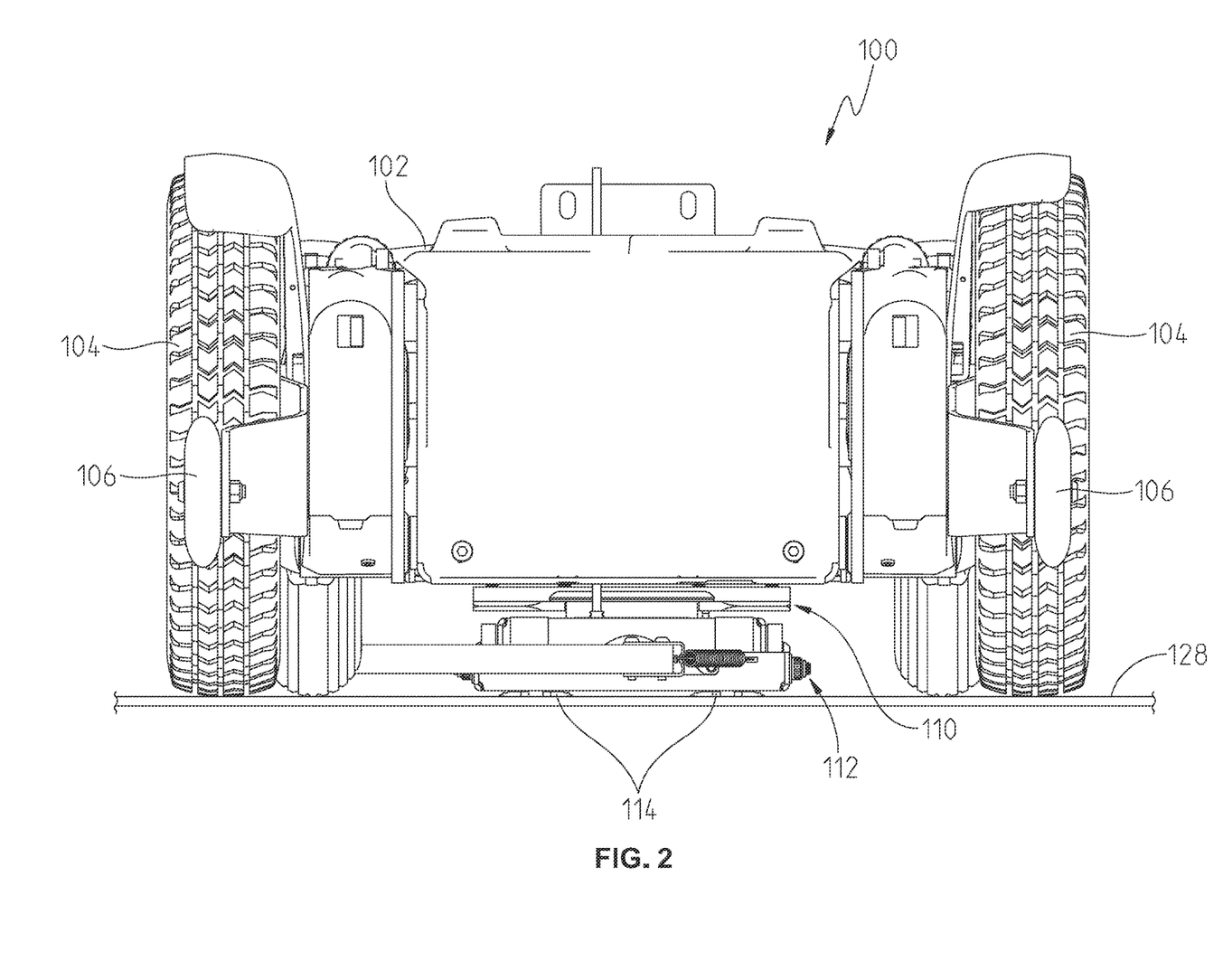
FIG. 2 is a perspective view of the wheelchair coupled to the docking system.

In FIG. 2, the bottom portion of the wheelchair 100 is better shown. Here, the wheelchair 100 has a bottom surface 116 to which the coupling device 110 is connected via one or more fasteners. The wheelchair 100 may also include a sensor 117 to detect the position of the coupling device 110 relative to the floor on which the wheels 104 are resting. In other words, the sensor 117 detects the clearance distance of the wheelchair 100. The sensor 117 may be a rotational pin configured to measure relative position of components of the wheelchair 100 or any other position sensor suitable for detecting the clearance distance. The sensor 117 may be operatively coupled to the wheelchair controller 120 to send signals thereto indicative of the position of the coupling device 110 relative to the floor 128 or other ground surface (i.e. the clearance distance).

The coupling device 110 may be a substantially U-shaped bracket 200 formed by a first leg 202 and a second leg 204. The first and second legs 202, 204 are spaced from one another to define an opening 206 therebetween. In FIG. 2, the opening 206 is oriented towards a front end 208 of the wheelchair 100 rather than a rear end 210; however, in some embodiments the opposite may be true.

The opening 206 in the bracket 200 is configured to engage with the docking system 112. The docking system 112 may include a frame 216 and the coupler mechanism 218 as shown in FIG. 2. The coupler mechanism 218 may comprise a neck portion that extends upwardly from the frame 216 and terminates at a disk-shaped top portion 222. As the wheelchair 100 is moved into engagement with the docking system 112, the bracket 200 comes into contact with the coupler mechanism 218. In particular, the coupler mechanism 218 is received within the opening 206 of the coupling device 110, and the first leg 202 and second leg 204 are received within a space defined between the frame 216 of the docking system 112 and the disk-shaped top portion 222 of the coupler mechanism 218 adjacent the neck portion. In the engaged position, the first leg 202 and second leg 204 may be in close proximity or contact with the neck portion of the coupler mechanism 218.

To maintain the wheelchair 100 engaged with the docking system 112, the docking system 112 may further include a retractable locking pin 224. The locking pin 224 may have an angled surface which comes into contact with a first surface 226 of the bracket 200 causing the locking pin 224 to be pushed downwardly into an opening. Once the bracket 200 clears the locking pin 224, a spring may bias the locking pin 224 to its upward position of FIG. 2. In the upward position, the bracket 200 is retained between the coupler mechanism 218 and the locking pin 224. This connection between the wheelchair 100 and docking system 112 may establish a first of at least two latching mechanisms between the docking system 112 and the wheelchair 100.

Figure 3:
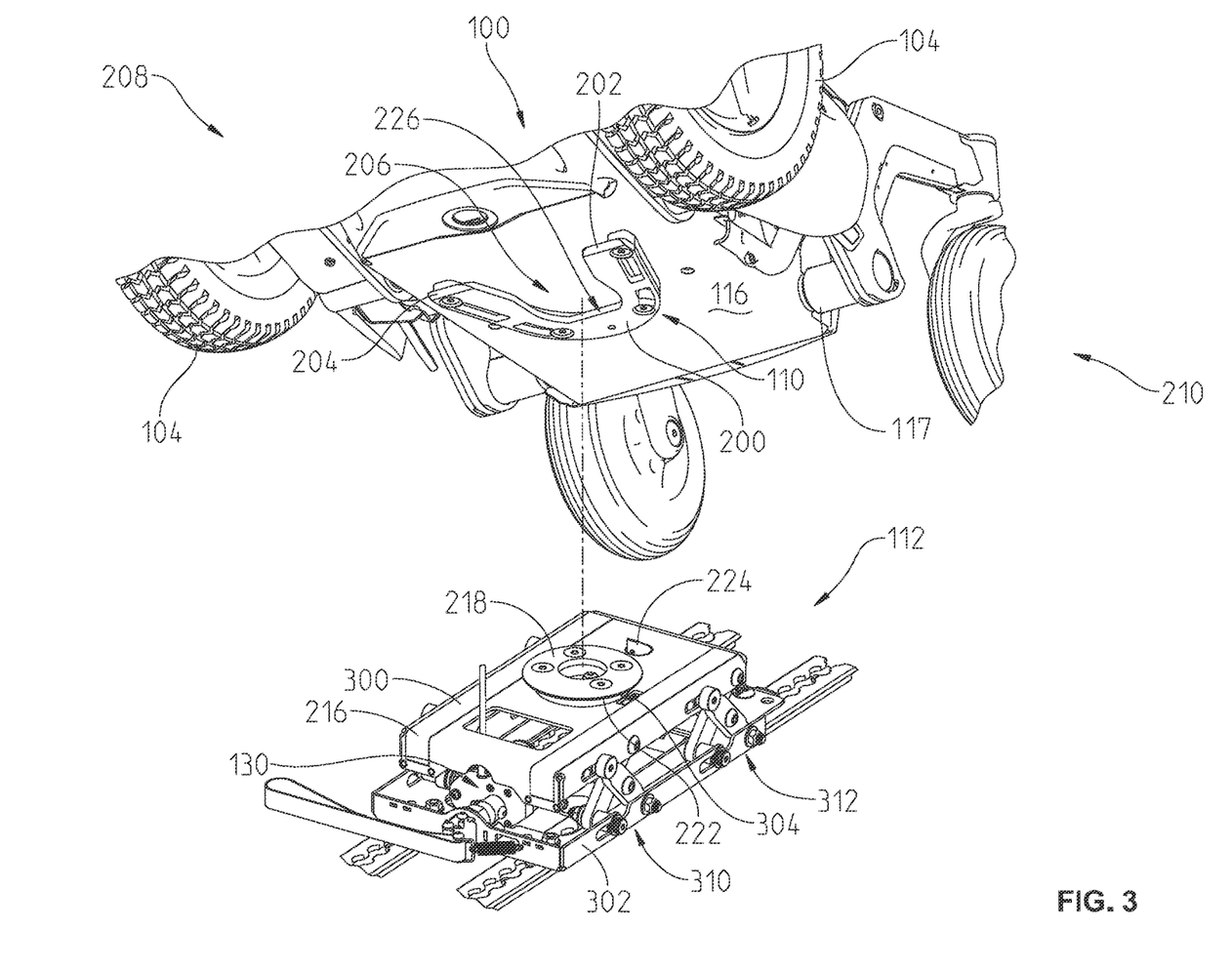
FIG. 3 is a perspective view of the docking system and the wheelchair showing that a coupler mechanism of the docking system may align with and couple to a coupling device of the wheelchair.

As shown in FIG. 3, the docking system 112 includes a top portion 300 and a bottom portion 302. The height of the bottom portion 302 is fixed relative to the floor 128 when the docking system 112 is coupled to the floor 128 of the vehicle 124. The docking system 112 includes front and rear scissor mechanisms 310, 312 coupled to the top and bottom portions 300, 302 of the docking system 112. The actuator 130 extends and retracts longitudinally relative to the frame 216 of the docking system 112. The actuator 130 is coupled to the scissor mechanisms 310, 312 such that movement of the actuator 130 longitudinally causes the scissor mechanisms 310, 312 to move between an open state and closed state to adjust the height of the top portion 300 of the docking system 112 relative to the floor 128. The coupler mechanism 218 is fixed to the frame top portion 300 of the docking system 112; therefore, movement of the actuator 130 ultimately adjusts the height of the coupler mechanism 218 relative to the floor 128 of the vehicle 124.

The docking system may include a sensor 304 that detects whether the wheelchair 100 is engaged by the coupler mechanism 218 and locking pin 224. The sensor 304 may send a signal to the dock controller 122 when the wheelchair 100 is engaged by the coupler mechanism 218 and locking pin 224, which causes the dock controller 114 to automatically trigger the actuator 130 to reduce the height of (i.e. lower) the top portion 300 relative to the bottom portion 302. The actuation of the docking system 112 to a lowered position functions as a second latching mechanism for holding the wheelchair 100 more securely during operation of the vehicle 124.

The user occupying the wheelchair 100 or another user may move the locking pin 224 to a retracted positon by pulling a pull cord to manually move the locking pin 224 or via the computing device 134. If the user uses the computing device 134, the computing device 134 sends a signal to the data processing system 136 to indicate the locking pin 224 is to be moved to the retracted position. The data processing system 136 sends a signal to the dock controller 122 indicate the locking pin 224 is to be moved to the retracted position.

In some embodiments, the computing device may send the signal directly to the dock controller 122, (e.g., via a wireless communication network connecting the two components 134, 122). In any event, the dock controller 122 sends a signal to a second actuator (not shown in FIG. 3), which may be referred to as a second actuator 600, to move the locking pin 224 to the retracted position. When the locking pin 224 is in the retracted position, the wheelchair 100 may disengage from the docking system 112.

In some embodiments, the computing device 134 sends a signal to the data processing system 136 or to the dock controller 122 to indicate the locking pin 224 is to be moved to the retracted position at some point in the future (for example, when the vehicle 124 arrives at a bus stop or other known destination). In this case, the data processing system 136 receives a signal from the computing device 134 indicating that the docking system 112 is selectable by users who may select (or reserve) the docking system 112 for some point in the future (for example, at or subsequent to the indicated bus stop or other known destination.

After the wheelchair 100 is disengaged from the docking system 112, the dock controller 122 sends a signal to the data processing system 136 indicating that the docking system 112 is selectable by users.

In some embodiments, the docking system 112 is one of a plurality of docking systems each positioned in the interior 126 of the vehicle 124 and included in the wheelchair system 10. The data processing system 136 may send signals to and receive signals from a plurality of dock controllers each operatively coupled to a corresponding docking system. In some embodiments, a single dock controller is operatively coupled to each of the plurality of docking systems. The data processing system 136 may receive signals indicating the selectability of each of the plurality of docking systems, respectively. The selectability of each of the plurality of docking systems, respectively, may be displayed to a user via the computing device 134.

In some embodiments, the vehicle 124 is one of a plurality of vehicles each having one or more docking systems positioned in the interior thereof. Each vehicle is included in the wheelchair system 10. The data processing system 136 may receive signals indicating the selectability of each of the plurality of docking systems positioned in each of the plurality of vehicles. The selectability of each of the plurality of docking systems positioned in each of the plurality of vehicles may be displayed to a user via the computing device 134. A user may select any selectable docking system to reserve the selected docking system for the user, as described herein.

While exemplary embodiments incorporating the principles of the present disclosure have been disclosed herein, the present disclosure is not limited to the disclosed embodiments. Instead, this application is intended to cover any variations, uses, or adaptations of the disclosure using its general principles. For instance, the present disclosure is not limited to the modification of a purchased OEM vehicle, but can be incorporated into the OEM vehicle when manufactured. Further, this application is intended to cover such departures from the present disclosure as come within known or customary practice in the art to which this disclosure pertains and which fall within the limits of the appended claims.

The invention claimed is:

1. A wheelchair system comprising:
a coupling device for a wheelchair;
a docking system configured to be mounted to a vehicle, wherein the docking system includes a coupler mechanism configured to engage with the coupling device and an actuator configured to adjust a height of the coupler mechanism;
a dock controller configured to be operatively coupled to the docking system; and
wherein the dock controller is configured to: (a) receive a signal indicative of a distance between the coupling device and a floor of the vehicle, and (b) send a signal to the actuator of the docking system to adjust the height of the coupler mechanism based on the signal indicative of the distance prior to the wheelchair being disposed in a securement location whereby the coupler mechanism may engage with the coupling device simultaneously with the wheelchair entering the securement location.

2. The wheelchair system of claim 1, wherein the dock controller is configured to: receive a unique identifier associated with the wheelchair, wherein the unique identifier comprises at least one of: a name of the wheelchair, a pairing code associated with the wheelchair, and a MAC address associated with the wheelchair; operatively connect to a wheelchair controller of the wheelchair; and receive the signal indicative of the distance from the wheelchair controller.

3. The wheelchair system of claim 1, wherein:
the wheelchair system further comprises the vehicle;
the docking system is coupled to the floor; and
the wheelchair further includes:
a set of wheels configured to rest on the floor of the vehicle,
a bottom surface supported above the floor by the set of wheels, and
the coupling device positioned on the bottom surface of the wheelchair.

4. The wheelchair system of claim 3 further comprising a wheelchair controller operatively coupled to the wheelchair, wherein the wheelchair controller is configured to provide the signal indicative of the distance to the dock controller.

5. The wheelchair system of claim 4 wherein the dock controller is configured to operatively connect to the wheelchair controller via a wireless communication network.

6. The wheelchair system of claim 3, wherein the distance is adjustable.

7. The wheelchair system of claim 1, wherein the dock controller is configured to send a signal to the actuator of the docking system to reduce the height of the coupler mechanism after the coupler mechanism of the docking system is engaged with the coupling device of the wheelchair, to further secure the wheelchair to the docking system.

8. The wheelchair system of claim 1 further comprising a computing device and a data processing system configured to communicate with the dock controller and the computing device, wherein:
the computing device is configured to send a signal to the data processing system indicating that the docking system has been selected; and
the dock controller is configured to send a signal to the data processing system indicating that the docking system is not selectable when the coupler mechanism of the docking system is engaged with the coupling device of the wheelchair.

9. The wheelchair system of claim 8, wherein after the coupling device of the wheelchair is disengaged from the coupler mechanism of the docking system, the dock controller is configured to send a signal to the data processing system indicating that the docking system is selectable.

10. The wheelchair system of claim 1 further comprising the vehicle, wherein the docking system is one of a plurality of docking systems coupled to the vehicle;
   wherein the vehicle is one of a plurality of vehicles each having a plurality of docking systems; and
   wherein a computing device is configured to display the selectability of each of the plurality of docking systems of each of the pluralities of vehicles.

11. The wheelchair system of claim 1 further comprising a sensor configured to detect the distance.

12. The wheelchair system of claim 1, wherein the dock controller is further configured (a) to continuously receive the signal indicative of a clearance distance of the coupling device as the wheelchair approaches the securement location, and (b) continuously send the signal to the actuator of the docking system to adjust the height of the coupler mechanism based on the signal indicative of the clearance distance of the coupling device prior to the wheelchair being disposed in a securement location whereby the coupler mechanism may engage with the coupling device simultaneously with the wheelchair entering the securement location.

13. A method of operation for a wheelchair system comprising:
   receiving, with a dock controller that is operatively coupled to a docking system for a wheelchair, a signal indicative of a distance between a coupling device on the wheelchair and a floor of a securement location; and
   adjusting a height of a coupler mechanism on the docking system prior to the wheelchair being disposed in the securement location based on the signal indicative of the distance whereby the coupler mechanism may engage with the coupling device simultaneously with the wheelchair entering the securement location.

14. The method of claim 13, further comprising:
   operatively connecting the dock controller with a wheelchair controller of the wheelchair via a wireless communication network, whereby the dock controller receives the signal indicative of the distance from the wheelchair controller the wheelchair controller.

15. The method of claim 14, further comprising:
   sending a signal to a computing device to request authorization for connecting the dock controller with the wheelchair controller via the wireless communication network, prior to operatively connecting the dock controller with the wheelchair controller via the wireless communication network.

16. The method of claim 13, further comprising:
   selecting the docking system with a computing device;
   sending a signal to a data processing system to indicate that the docking system was selected; and
   indicating that the docking system is no longer selectable.

17. The method of claim 13, wherein the wheelchair includes a set of wheels configured to rest on the floor, a bottom surface supported above the floor by the set of wheels, and the coupling device positioned on the bottom surface of the wheelchair.

18. The method of claim 17, further comprising:
   securing the wheelchair to the docking system;
   wherein securing the wheelchair to the docking system includes:
      engaging the coupler mechanism of the docking system with the coupling device of the wheelchair; and
      reducing the height of the coupler mechanism of the docking system, after the coupler mechanism of the docking system is engaged with the coupling device of the wheelchair, to reduce the distance.

19. The method of claim 18, further comprising:
   adjusting the distance.

20. The method of claim 17, further comprising:
   securing the wheelchair to the docking system;
   operatively connecting the dock controller with a wheelchair controller via a wireless communication network; and
   sending signals indicative of the distance through a secure communication channel, continuously, while the wheelchair controller is operatively connected to the dock controller.

21. The method of claim 13, further comprising:
   securing the wheelchair to the docking system;
   disengaging the wheelchair and the docking system; and
   sending a signal to a data processing system to indicate that the docking system from which the wheelchair was disengaged is available to be selected.

22. The method of claim 13 further comprising sensing the distance.

23. A method of operation of a docking system for a wheelchair comprising:
   receiving, with a dock controller operatively coupled to the docking system, a unique identifier associated with the wheelchair;
   sending an encryption key to a wheelchair controller operatively coupled to the wheelchair, wherein the encryption key is associated with a secure communication channel between the wheelchair controller and the dock controller;
   adjusting a height of a coupler mechanism on the docking system based on a signal received from the wheelchair controller through the secure communication channel prior to the wheelchair being disposed in a securement location, the signal being indicative of a distance between a coupling device on the wheelchair and a floor of the securement location, whereby the coupler mechanism may engage with the coupling device simultaneously with the wheelchair entering the securement location.

* * * * *